United States Patent
Koch et al.

(10) Patent No.: US 11,432,705 B2
(45) Date of Patent: Sep. 6, 2022

(54) SYSTEM FOR ENDOSCOPIC IMAGING AND METHOD FOR PROCESSING IMAGES

(71) Applicant: Helmholtz Zentrum Munchen Deutsches Forschungszentrum Fur Gesundheit Und Umwelt (GMBH), Neuherberg (DE)

(72) Inventors: Maximilian Koch, Munich (DE); Vasilis Ntziachristos, Munich (DE)

(73) Assignee: Helmholtz Zentrum Munchen Deutsches Forchungszentrum fur Gesundheit und Umwelt GMBH

( * ) Notice: Subject to any disclaimer, the term of this patent is extended or adjusted under 35 U.S.C. 154(b) by 306 days.

(21) Appl. No.: 16/624,593

(22) PCT Filed: Jun. 22, 2018

(86) PCT No.: PCT/EP2018/066756
§ 371 (c)(1),
(2) Date: Dec. 19, 2019

(87) PCT Pub. No.: WO2018/234545
PCT Pub. Date: Dec. 27, 2018

(65) Prior Publication Data
US 2020/0121162 A1   Apr. 23, 2020

(30) Foreign Application Priority Data
Jun. 22, 2017 (EP) ..................... 17177344

(51) Int. Cl.
*A61B 1/00* (2006.01)
*A61B 1/005* (2006.01)
(Continued)

(52) U.S. Cl.
CPC ........ *A61B 1/00009* (2013.01); *A61B 1/0005* (2013.01); *A61B 1/00006* (2013.01); (Continued)

(58) Field of Classification Search
CPC combination set(s) only.
See application file for complete search history.

(56) References Cited

U.S. PATENT DOCUMENTS

| 2008/0267472 A1* | 10/2008 | Demos | A61B 1/00009 |
| | | | 382/128 |
| 2016/0278678 A1* | 9/2016 | Valdes | A61B 5/1459 |

FOREIGN PATENT DOCUMENTS

JP             07250804 A  * 10/1995  ............. A61B 1/043

* cited by examiner

*Primary Examiner* — Timothy J Neal
(74) *Attorney, Agent, or Firm* — Dorsey & Whitney LLP

(57) ABSTRACT

The invention relates to a system for endoscopic imaging comprising a light source configured to generate light and an, in particular rigid, insertion portion configured to be inserted into an object and comprising a distal end, a proximal end and at least one light guiding path. The system further comprises a first imaging device mounted at the proximal end of the insertion portion and optically coupled to the light guiding path, the first imaging device comprising a plurality of first detecting elements exhibiting a first sensitivity to light. A flexible guiding portion comprising a distal end and a proximal end is provided to guide a second part of the light emanating from the medium from the distal end of the guiding portion to the proximal end of the guiding portion. A second imaging device provided at the proximal end of the flexible guiding portion comprises a plurality of second detecting elements exhibiting a second sensitivity to light, the second sensitivity of the second detecting elements being higher than the first sensitivity of the first detecting elements. A control unit is configured to derive at least one third image of the medium based on image data of the at least one first image of the medium and image data of the at least one second image of the medium. The invention further relates to a corresponding method for processing images.

12 Claims, 4 Drawing Sheets

(51) Int. Cl.
*A61B 1/04* (2006.01)
*A61B 1/05* (2006.01)
*G06T 7/00* (2017.01)

(52) U.S. Cl.
CPC ............ *A61B 1/0051* (2013.01); *A61B 1/043* (2013.01); *A61B 1/05* (2013.01); *G06T 7/0012* (2013.01); *G06T 2207/20201* (2013.01); *G06T 2207/20221* (2013.01)

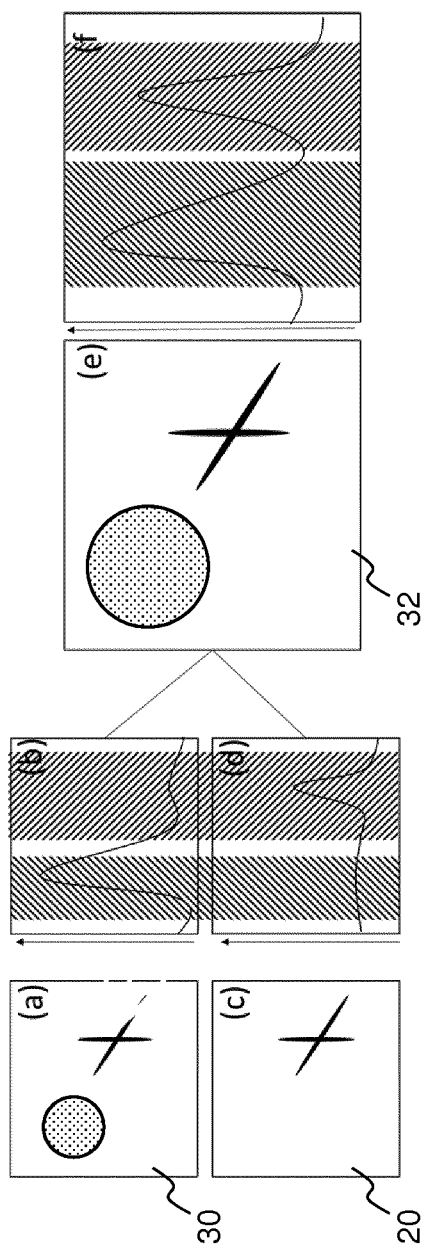

SYSTEM FOR ENDOSCOPIC IMAGING AND METHOD FOR PROCESSING IMAGES

The present invention relates to a system for endoscopic imaging and a corresponding method for processing images.

Optical imaging is widely employed in medicine during endoscopic procedures, e.g. in surgery, ophthalmology and other applications. Healthy and diseased tissues exhibit differences in several properties, e.g. structural, compositional, metabolic, molecular and cellular properties, which can be optically detected. Detection is based either on intrinsic tissue chromophores such as haemoglobin or melanin or extrinsically administered agents (e.g. fluorochromes) which can in-vivo stain physiological, cellular or molecular features (e.g. perfusion, permeability, inflammation, receptor distribution etc). Local or systemic administration of agents with specificity to cellular and subcellular tissue and disease biomarkers can alter the optical properties of healthy and diseased tissue in different ways resulting in visualization of lesions with high contrast with the background healthy tissues. Recent studies indicate that the use of externally administered fluorescent agents is a highly promising approach since fluorescence signals can provide high contrast. For example, engineered agents can be very sensitive and specific in cancer detection by targeting specific molecular features of carcinogenesis and tumor lesions. This information can be combined with contrast from intrinsic tissue chromophores like haemoglobin or melanin to yield accurate predictive, diagnostic and/or interventional guidance.

The majority of optical imaging systems employed clinically today are based on a photographic or video approach employing reflectance imaging, also termed epi-illumination. The term fluorescence imaging is also broadly employed to describe photography or video approaches using a filter to reject excitation light and register only fluorescence photons on the camera. Often two or multiple camera systems are employed, some cameras detecting color images, some cameras fluorescence images.

Other designs have been proposed that utilize imaging at multiple wavelengths, also referred to as spectral imaging, multispectral imaging or hyperspectral imaging, which can be employed to resolve different optical absorbers or differentiate auto-fluorescence from a fluorochrome of interest.

The invention is based on the problem to provide an improved system for endoscopic imaging and method for processing images, in particular allowing for both high sensitivity imaging and easy handling.

The problem is solved by the system and method according to the independent claims.

A system for endoscopic imaging according to an aspect of the invention comprises a light source configured to generate light and an insertion portion configured to be inserted into an object and comprising a distal end, a proximal end and at least one light guiding path configured to guide the generated light to the distal end of the insertion portion and to guide light emanating from a medium within the object to the proximal end of the insertion portion. The system further comprises a first imaging device mounted at the proximal end of the insertion portion and optically coupled to the light guiding path, the first imaging device comprising a plurality of first detecting elements, the first detecting elements exhibiting a first sensitivity to light and being configured to detect a first part of the light emanating from the medium to obtain a first image of the medium exhibiting a first spatial resolution. Further, a flexible guiding portion comprising a distal end and a proximal end is provided, the distal end of the guiding portion being optically coupled to the light guiding path. The guiding portion is configured to guide a second part of the light emanating from the medium from the distal end of the guiding portion to the proximal end of the guiding portion. Additionally, a second imaging device is provided at the proximal end of the flexible guiding portion and comprises a plurality of second detecting elements, the second detecting elements exhibiting a second sensitivity to light and being configured to detect the second part of the light emanating from the medium to obtain a second image of the medium exhibiting a second spatial resolution, the second sensitivity of the second detecting elements being higher than the first sensitivity of the first detecting elements.

In a method according to another aspect of the invention, images generated by a system for endoscopic imaging are processed, wherein the system comprises a light source configured to generate light, an, in particular rigid, insertion portion configured to be inserted into an object and comprising a distal end, a proximal end and at least one light guiding path configured to guide the generated light to the distal end of the insertion portion and to guide light emanating from a medium within the object to the proximal end of the insertion portion, a first imaging device mounted at the proximal end of the insertion portion and optically coupled to the light guiding path, the first imaging device comprising a plurality of first detecting elements, the first detecting elements exhibiting a first sensitivity to light and being configured to detect a first part of the light emanating from the medium to obtain at least one first image of the medium exhibiting a first spatial resolution, a flexible guiding portion comprising a distal end and a proximal end, the distal end of the guiding portion being optically coupled to the light guiding path, and being configured to guide a second part of the light emanating from the medium from the distal end of the guiding portion to the proximal end of the guiding portion, and a second imaging device provided at the proximal end of the flexible guiding portion and comprising a plurality of second detecting elements, the second detecting elements exhibiting a second sensitivity to light and being configured to detect the second part of the light emanating from the medium to obtain at least one second image of the medium exhibiting a second spatial resolution, the second sensitivity of the second detecting elements being higher than the first sensitivity of the first detecting elements, and wherein the method comprises deriving at least one third image of the medium based on image data of the at least one first image of the medium and image data of the at least one second image of the medium by correcting image data of the at least one second image of the medium for motion of the insertion portion and the medium relative to each other based on image data of the at least one first image of the medium, and/or combining, in particular fusing, image data of the at least one first image of the medium and image data of the at least one second image of the medium to obtain the at least one third image, wherein the range, in particular a ratio or difference, between a highest image data value and a lowest image data value contained in the image data of the at least one third image is larger than the range between a highest image data value and a lowest image data value contained in each of the image data of the at least one first image and the image data of the at least one second image.

Preferably, the system for endoscopic imaging provides a first and a second imaging device which are arranged spatially separated from each other. In particular, the first imaging device, e.g. a first camera exhibiting a first sensitivity to light, is arranged at a proximal end of an insertion portion, e.g. an endoscope, which is configured to be at least partially inserted into an object, and optically coupled to a light guiding path of the insertion portion configured to convey light from a distal end of the insertion portion to the proximal end of the insertion portion or vice versa. The second imaging device, e.g. a second camera exhibiting a second sensitivity to light which is higher than the first sensitivity of the first camera, is arranged at a proximal end of a flexible guiding portion, the distal end of which being optically coupled to the light guiding path of the insertion portion as well. Thereby, light generated by a light source, which is preferably arranged in the region of the second imaging device and optically coupled to the proximal end of the flexible guiding portion as well or, alternatively, arranged in the region of the first imaging device and optically coupled to the light guiding path, is conveyed by the light guiding path to a medium inside the object, and light emanating, e.g. due to reflection, scattering and/or luminescence, from the medium is conveyed to the first imaging device and to the second imaging device without the necessity of the second imaging device and, if applicable, the light source, being arranged at the proximal end of the insertion portion.

By means of the flexible guiding portion the first imaging device and the second imaging device are spatially separated from each other, so that even a heavy and bulky high-sensitivity second imaging device can be included into the system without limiting the handiness and/or handling of the insertion portion and the available space at the proximal end of the insertion portion.

Further, the arrangement described above allows for simultaneous acquisition of images by the first and the second imaging device such that real-time imaging can be performed.

Moreover, providing two different imaging devices for endoscopic imaging, wherein the second imaging device is not limited by size or weight, allows for flexible imaging and provides a user, e.g. a physician, with increased information. For example, a first, lightweight camera which is configured to generate high-resolution color images can be directly optically coupled to the light guiding path of a laparoscope, e.g. by mounting the first camera at the proximal end of the light guiding path, and a second, heavyweight camera configured to capture fluorescence images at high sensitivity can be indirectly optically coupled to the light guiding path via the flexible guiding portion. Because the second camera is not directly mounted at the laparoscope, the distal end of the laparoscope can be inserted into the object, e.g. a human body, easily and positioned therein with high precision, regardless of the weight and/or size of the second camera. Light generated by the light source is conveyed through the endoscope and illuminates tissue in a region of the distal end of the laparoscope, such that light emanating from the tissue in response thereof is detected by the first and the second camera, preferably simultaneously.

In summary, the invention provides an improved system for endoscopic imaging and method for processing images, in particular allowing for high sensitivity imaging and easy handling.

Within the meaning of the invention, the term "endoscopic imaging" relates to any kind of imaging in which an inward or interior part of an organism and/or any object or cavity is imaged. For example, endoscopic imaging includes, but is not limited to, laparoscopic, thoracoscopic, esophagoscopic, gastroscopic, coloscopic and arthroscopic imaging.

According to a preferred embodiment of the invention, the first spatial resolution of the first image is higher than the second spatial resolution of the second image. In particular, the first imaging device comprises an imaging sensor, which is particularly lightweight and provides a particularly high spatial resolution at small dimensions. By this means, optical images of the medium of the object with both high sensitivity (via second imaging device) and high spatial resolution (via first imaging device) can be obtained simultaneously.

According to another preferred embodiment of the invention, the system comprises a coupling element provided at the proximal end of the insertion portion, the coupling element being configured to optically couple both the first imaging device and the distal end of the flexible guiding portion to the light guiding path of the insertion portion. By this means, the first part of the light can be easily and reliably guided from the light guiding path to the first imaging device, while at the same time the second part of the light can be easily and reliably guided from the light guiding path, via the flexible guiding portion, to the second imaging device. In particular, the coupling element allows for simultaneous transmission of the light emanating from the light guiding path at the proximal end of the insertion portion towards the first imaging device and the second imaging device such that real-time imaging with particularly high sensitivity and spatial resolution becomes possible.

According to yet another embodiment of the invention, the coupling element comprises a semi-transparent or dichroic mirror configured to reflect or transmit the first part of the light emanating from the medium to the first detecting elements, and to transmit or reflect, respectively, the second part of the light emanating from the medium to the second detecting elements. This is particularly advantageous if the first part of the light comprises a different polarization than the second part of the light or if the first part of the light comprises a different wavelength or spectrum of wavelengths than the second part of the light. This allows for particularly reliable separation of the first part of the light from the second part of the light to be detected by the first and second imaging device, respectively.

According to yet another embodiment of the invention the insertion portion is rigid. Because of the lightweight low-sensitivity first camera mounted at the proximal end of the rigid insertion portion, the insertion portion is also lightweight and slim and can be easily handled and inserted into a soft object, such as a human or animal body, and/or precisely positioned in the soft object such that areas of interest, e.g. where physician suspects diseased tissue, can be imaged reliably.

Alternatively, the insertion portion or at least a part thereof is flexible. Likewise, the lightweight low-sensitivity first camera mounted at the proximal end of the flexible insertion portion allows for an easy handling of the lightweight and slim insertion portion, e.g. when inserting the insertion portion into wound or crooked cavities of an object as with gastroscopy or coloscopy, and reliable imaging of the inner structures of such cavities.

In yet another embodiment of the invention, the first part of the light emanating from the medium corresponds to light reflected by the medium in response to an irradiation of the medium with the generated light. Preferably, the first imaging device comprises an optical filter configured to transmit light being reflected by the medium and to suppress all other light emanating from the medium, e.g. due to its specific polarization or wavelength. By this means, the sensitivity of the first imaging device for light reflected by the medium can be increased such that high quality reflection images of the medium in the object can be reliably acquired.

In particular, the second part of the light reflected by the medium corresponds to a diagnostic image-forming signal, including but not limited to a, in particular high resolution, color image.

In yet another embodiment of the invention, the second part of the light emanating from the medium corresponds to luminescence, Raman-scattered or scintillation light emitted by the medium in response to an irradiation of the medium with the generated light or radiation. Preferably, the second imaging devices comprises an optical filter configured to transmit luminescence, Raman-scattered or scintillation light emanating from the medium and to suppress other light emanating from the medium, e.g. due to its specific polarization or wavelength. By this means, the sensitivity of the second imaging device for luminescence, Raman-scattered or scintillation light emanating from the medium can be increased such that high-quality luminescence or scintillation images, respectively, of the medium in the object can be reliably acquired.

Within the meaning of present invention, the term "luminescence" includes, but is not limited to, fluorescence, phosphorescence, bioluminescence, chemoluminescence, Raman emission, radio-luminescence (e.g. Cherenkov radiation).

In particular, the second part of the light emanating from the medium corresponds to a diagnostic image-forming signal including, but not limited to, luminescence or light emanating from a scintillator in correspondence to incident nuclear radiation.

In yet another embodiment of the invention, the light guiding path of the insertion portion comprises a tubular optical path and at least one relay lens configured to relay an image of the medium through the tubular optical path to the first detecting elements of the first imaging device. Preferably, the first relay lens is arranged and/or mounted at the proximal end of the insertion portion and/or the distal end of the insertion portion and images the medium onto the first detecting elements via the coupling element. The tubular optical path may comprise a coherent fiber bundle. Alternatively, the tubular optical path comprises a cavity, preferably filled with a coupling medium, e.g. gas and/or liquid, to reliably convey the light emanating from the medium in response to illumination of the medium with light. By this means, the medium near the distal end of the insertion portion can be reliably and precisely imaged by the first imaging device.

In yet another embodiment of the invention, the flexible guiding portion comprises an optical fiber bundle, preferably a coherent optical fiber bundle, configured to relay an image of the medium through the optical fiber bundle to the second detecting elements of the second imaging device. Preferably, the second imaging device is configured to compensate for a possible loss of intensity of the second part of the light in the fiber bundle with an increased sensitivity of the second imaging device. By this means, the insertion portion can be easily and flexibly handled without adding the weight of the second imaging device to the insertion portion, while optical images can be obtained by the second imaging device with high sensitivity.

According to another aspect of the invention, the system further comprises a control unit configured to derive a third image of the medium based on image data of the first image of the medium and image data of the second image of the medium. The third image may contain information of both the first and the second image and/or information derived from a combination of the first and the second image. In this way, third images with enhanced diagnostic conclusiveness can be obtained.

According to yet another aspect of the invention, the control unit is further configured to derive the third image of the medium by correcting image data of the, preferably high-sensitivity, second image of the medium for a possible motion of the insertion portion and the medium relative to each other based on image data of the, preferably high-resolution, first image of the medium. By this means, particularly conclusive diagnostic images, which do not suffer from motion blur or artifacts, of the medium are obtained.

Preferably, the control unit is configured to determine, in particular estimate, a two-dimensional motion field, which determines the velocity of the medium relative to the insertion portion or velocities of components and/or different regions of the medium relative to each other, by means of the, in particular high-resolution, first image. The control unit is preferably further configured to adapt the second image, in particular obtained with second detecting elements with high sensitivity, according to or based on the two-dimensional motion field. Additionally, the adapted second image may be further combined with successively obtained further second images, by which means second images may be accumulated such that the exposure time of the second images may be virtually prolonged.

Preferably, the control unit is further configured to determine, based on image data of the at least one first image of the medium, at least one two-dimensional motion field characterizing a velocity of the medium relative to the insertion portion or velocities of different regions of the medium relative to each other.

Preferably, the control unit is further configured to revert a motion-induced relative displacement of image data of the at least one second image based on the at least one two-dimensional motion field to obtain the at least one third image of the medium.

Preferably, the control unit is further configured to revert a motion-induced relative displacement of image data in each of two or more successively obtained second images based on the at least one two-dimensional motion field to obtain two or more adapted second images, and to combine the two or more adapted second images to obtain the at least one third image of the medium.

Preferably, the control unit is further configured to determine, based on image data of at least two successively obtained first images of the medium, a two-dimensional motion field, to revert a motion-induced relative displacement of image data in each of at least two successively obtained second images based on the two-dimensional motion field to obtain two or more adapted second images, and to combine the two or more adapted successively obtained second images to obtain the at least one third image of the medium.

Preferably, the motion field refers or corresponds to a description of motion-induced vector components, in particular regarding a distance and direction, of every picture element or image element (pixel) between two subsequently acquired first images.

Preferably, the control unit is further configured to weight image data of the second image with a factor $\alpha$ the magnitude of which depending on how much recent image data of the second image is, wherein image data of a more recently obtained second image is weighted with a higher factor than image data of a less recently obtained second image.

Preferably, the at least one first image of the medium being a color image and/or reflectance image of the medium, and the at least one second image of the medium being a fluorescent image of a fluorescence agent contained in the medium.

According to an alternative or additional aspect of the invention, the control unit is further configured to derive the third image of the medium by combining, in particular fusing, image data of the first image of the medium and image data of the second image of the medium. For example, by combining image data of a high-resolution color image of tissue (corresponding to the first image) with image data of a fluorescent image of a fluorescence agent (corresponding to the second image), a physician can easily identify disease tissue to which the fluorescence agent specifically binds. By this means, the dynamic range of the third image can be increased compared to the dynamic range of the first or second image.

Preferably, the term "dynamic range" refers to a range, a ratio or a difference between a highest image data value and a lowest image data value contained in the image data of the at least one first, second or third image, respectively. Accordingly, the range, ratio or difference between the highest image data value and the lowest image data value contained in the image data of the at least one third image is larger than the range, ratio or difference between the highest image data value and lowest image data value contained in each of the image data of the at least one first image and the image data of the at least one second image.

For example, image data value(s) contained in the image data of an image, in particular of the first, second and third image, may be pixel value(s), grey-level or grey scale value(s) and/or color or tonal value(s) at the pixel(s) of the image.

Preferably, the control unit is configured to spatially register regions, in particular pixels, of the first and second images with each other and to combine the regions such that high-sensitivity and high-resolution information complement each other in each of the corresponding regions in the third image.

Preferably, the control unit is configured to control the first imaging device and the second imaging device to detect the first part of the light emanating from the medium and the second part of the light emanating from the medium simultaneously.

Preferably, the first part of the light and the second part of the light emanate from the same region of interest of the medium or from overlapping regions of interest of the medium.

It is noted that the preferred embodiments of the system described above accordingly apply to the method for processing images. Thus, it is preferred that the method for processing images further comprises and/or performs one or more steps corresponding to one or more steps and/or functions executed by the control unit, i.e. steps and/or functions the control unit is configured to execute, as described above.

Further advantages, features and examples of the present invention will be apparent from the following description of following figures:

FIG. 4 shows an exemplary schematic of a second imaging mode.

Figure 1:
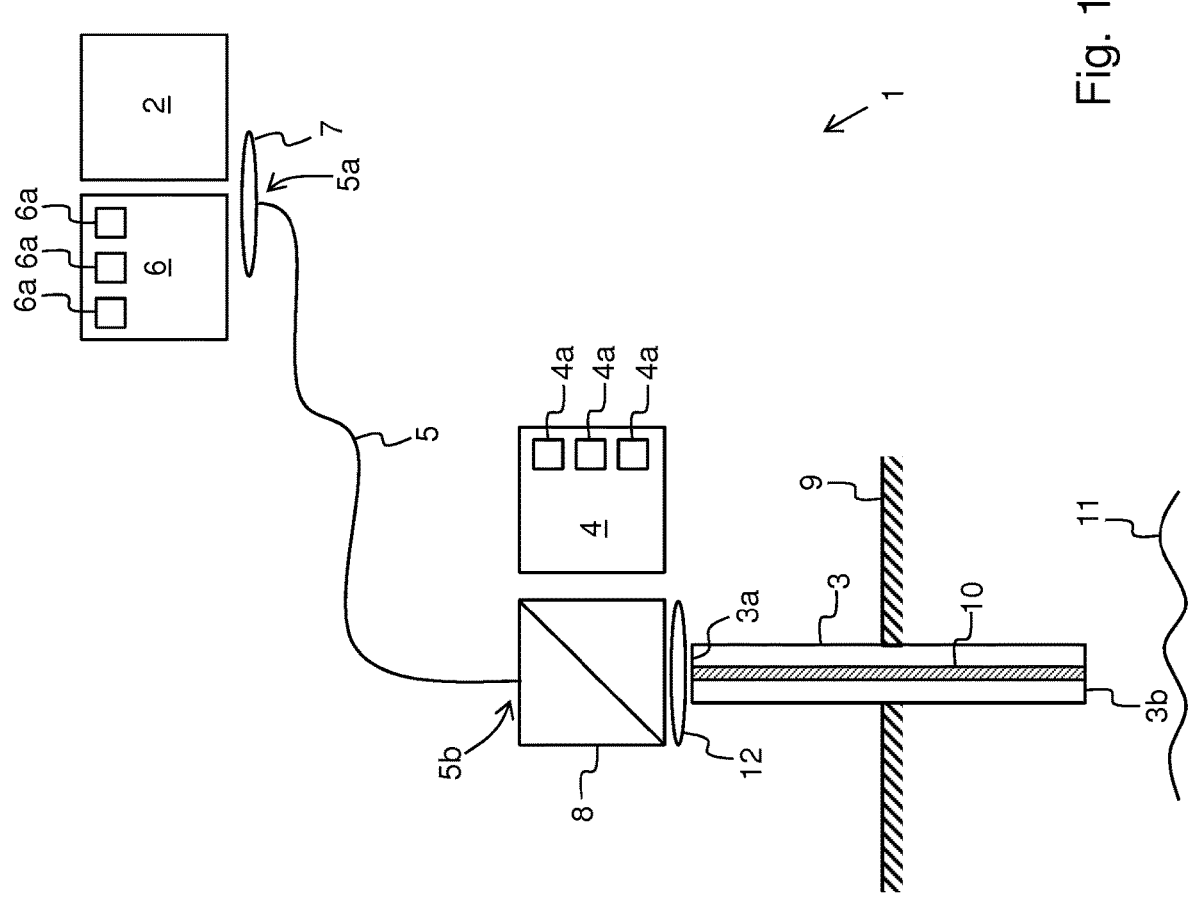
FIG. 1 shows an example of a system for endoscopic imaging.

FIG. 1 illustrates an exemplary system 1 for endoscopic imaging comprising a light source 2, an insertion portion 3, a first imaging device 4, a flexible light guiding portion 5 and a second imaging device 6.

The insertion portion 3 is configured to be inserted, at least partially, in particular with a distal end 3b, into an object 9. Preferably, the object 9, also referred to as sample, is a biological object, in particular a human or animal body or a part thereof. In particular, the sample comprises a medium 11, e.g. biological tissue or a part thereof. Accordingly, the system is particularly suited for medical imaging.

The light guiding portion 5, e.g. a coherent fiber bundle, is configured to convey light generated by the light source 2 to the insertion portion 3. Preferably, the light source 2 is optically coupled via a coupling device 7, e.g. a lens, to a proximal end 5a of the light guiding portion 5.

At its distal end 5b, the light guiding portion 5 is optically coupled to a light guiding path 10, e.g. an illumination port of a laparoscope, of the insertion portion 3 via a coupling element 8, e.g. a semi-transparent or dichroic encoded beam-splitter. The light guiding path 10 is configured to convey light from a proximal end 3a of the insertion portion 3 to the distal end 3b of the insertion portion 3 or vice versa.

The light generated by the light source 2 is transmitted by the coupling element 8 and conveyed through the light guiding path 10 such that it is emitted at the distal end 3b of the insertion portion 3, thereby illuminating the medium 11 of the object 9.

In response to the illumination, light emanates from the medium 11. Emanating light may be, e.g., reflected and/or scattered light and/or luminescent light which is excited in the medium 11 in response to the illumination. At least a part of the emanating light re-enters or enters, respectively, at the distal end 3b of the insertion portion 3 and is guided through the optical path 10 to the coupling element 8.

The coupling element 8 is preferably configured to split the light emanating from the medium 11 into a first part and a second part, wherein the first part of the light emanating from the medium 11 is relayed to the first imaging device 4 by means of a relay lens 12. The first imaging device 4 comprises a plurality of detecting elements 4a which are configured to detect the first part light to obtain a first image of the medium 11, preferably at a high spatial resolution.

In some embodiments, the coupling element 8 is configured to split the light emanating from the medium 11 dependent on properties of the light emanating from the medium 11, e.g. on photon energy or polarization, or a combination thereof.

The second part of the light emanating from the medium 11 is relayed to the second imaging device 6 by means of the flexible guiding portion 5. At the proximal end 5a of the flexible guiding portion 5, the second part of the light is detected by a plurality of detecting elements 6a of the second imaging device 6 such that a second image can be obtained, in particular with high sensitivity.

Additionally, further imaging devices can be arranged at the proximal end 3a of the insertion portion 3, i.e. optically coupled to the light guiding path 10 by means of the coupling element 8, and/or at the proximal end 5a of the flexible guiding portion 5 for obtaining multiple images of the medium 11.

Preferably, the first and second imaging devices 4, 6 are optical cameras, i.e. photon detection devices, e.g. a charged coupled device (CCD), a complementary metal-oxide-semiconductor (CMOS) sensor, an indium gallium arsenide (InGaAs) sensor. Preferably, the photon detection sensors, e.g. the CCD, CMOS and/or InGaAs sensors, are cooled.

In some embodiments, each of the first and second imaging devices 4, 6 may be constituted by more than one of the above-mentioned photon detection sensor types. In particular, a first plurality of detecting elements 4a, 6a of the first and/or second imaging device 4, 6 may correspond to detecting elements of a first type of the above-mentioned sensors, and a second plurality of detecting elements 4a, 6a of the first and/or second imaging device 4, 6 may correspond to detecting elements of a second type of the above-mentioned sensors. This allows for a flexible adaptation of the imaging devices 4, 6 to the requirements of practical applications where different signals corresponding to different components of the light emanating from the medium 11 exhibit different signal strengths and different dynamic ranges.

Preferably, the sensitivity of one or more of the independently sensitive CCD or CMOS or InGaAs sensors or corresponding detector elements, respectively, is automatically adapted, in particular through variable attenuation or amplification of the sample signals collected or the corresponding electrical signals.

In some embodiments, each of the at least two imaging devices 4, 6 is provided with a field filter being adjusted to a spectral sensitivity range of the respective imaging device 4, 6. Preferably changeable field filters are provided, by which the flexibility of the system is further improved.

Preferably, the light source 2 comprises at least a white light illumination arrangement configured to generate a broad illumination spectrum, and at least one target excitation illumination arrangement configured to generate at least one target wavelength. The target wavelength may be chosen from a large spectrum of wavelengths including the UV, visible, NIR and IR spectral regions, e.g. 0.2 μm-10 μm. Preferably, the use of excitation at NIR wavelengths, e.g. at wavelengths between 650 nm and 1100 nm, or the use of excitation at IR wavelengths between 1250 nm and 1350 nm allows seamless separation of white light images and near-infrared or infrared wavelengths. Due to reducing scatter in tissue with increasing wavelength, the use of far-NIR wavelengths, e.g. between 900 nm and 1350 nm, may lead to images of higher resolution.

Alternatively or additionally, temporal and spatial properties of light may be exploited as well. In particular, the generation of light patterns by the light source 2, e.g. spatially modulated light establishing areas of higher intensity and areas of lower intensity in the medium 11, may be utilized for achieving separation of optical properties, improving resolution or suppressing back-ground signals. Moreover, the generation of intensity-modulated light, e.g. light pulses, by the light source 2 can also be utilized to suppress background signals or simultaneously interleave multiple wavelengths. For example, modulation in the Hz-kHz range or so-called pulse interleaving, using pulses of different wavelengths, can allow simultaneous imaging at multiple wavelengths.

The overlapping information of different properties of light and/or tissue are preferably encoded or decoded, respectively, in time-interlaced fashion on either detection or illumination gating.

The system 1 for endoscopic imaging as illustrated in FIG. 1 may be employed to collect first and second images corresponding to different tissue properties, including polarization, auto-fluorescence, or fluorescence emanating from markers administered to the medium 11 for contrast enhancement. These images, also referred to as marker images, indicate intrinsic or extrinsic markers obtained in addition to the traditional color (reflectance) images obtained by the first imaging device 4.

The first part of the light emanating from the medium 11, also referred to as reflected light, is relayed onto the first imaging device 4, while the second part of the light emanating from the medium 11, also referred to as marker light, is relayed through the flexible guiding portion 5 onto the second imaging device 6, which is preferably particularly sensitive to the at least one wavelength of the marker light.

Preferably, both the reflection light and the marker light are collected simultaneously, thus allowing a real time processing of the multiple different images of the sample.

Figure 2:
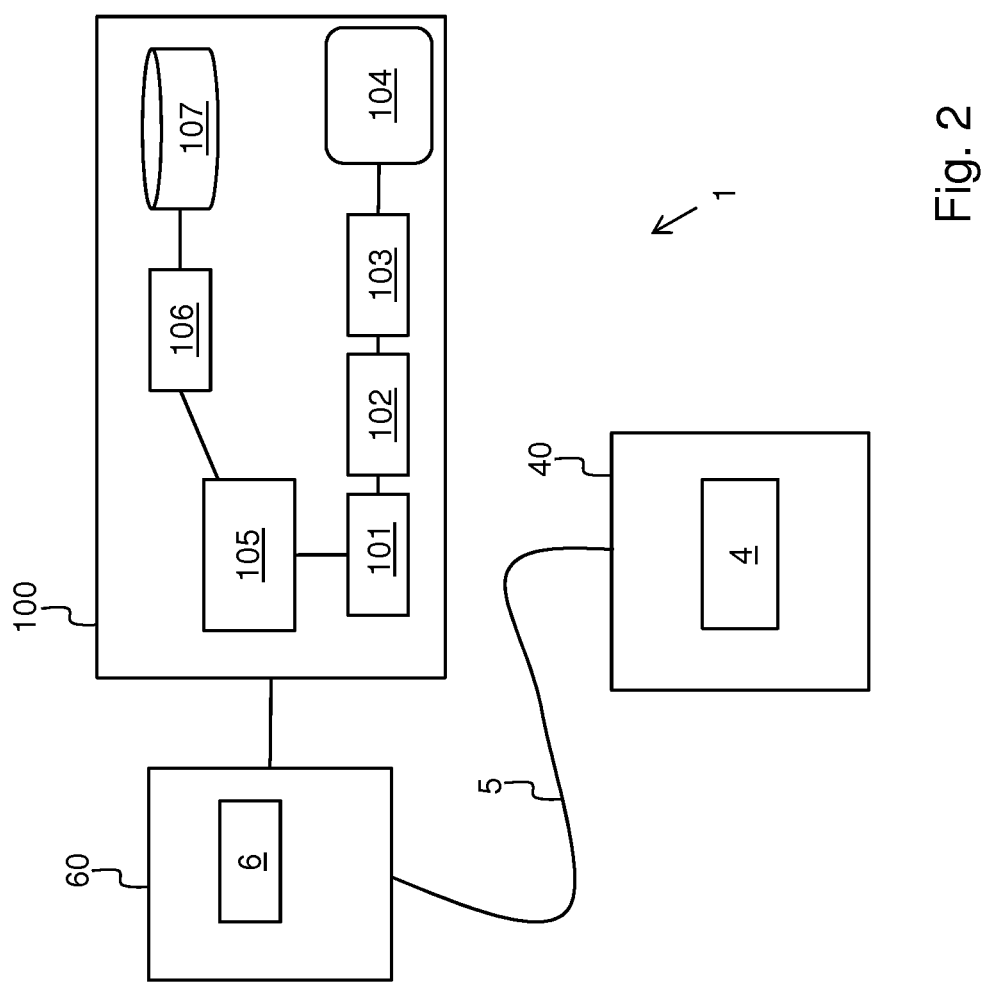
FIG. 2 shows an exemplary schematic of a system for endoscopic imaging.

FIG. 2 shows an exemplary schematic of a system 1 for endoscopic imaging, which is split into light-weight image acquisition hardware 40 comprising a first imaging device 4, and heavy-weight imaging acquisition hardware 60 comprising a second imaging device 6. Although not shown, either one or both of the image acquisition hardware 40, 60 may comprise additional imaging devices.

Preferably, the heavy-weight image acquisition hardware 60 is mounted on a mobile wheel-based rack (not shown). The image acquisition hardware 40, 60 entities are connected via flexible guiding portion 5, which may comprise a coherent optical fiber bundle and/or electrical power connection and/or data connection in order to optically and/or electrically couple image acquisition hardware 40 with image acquisition hardware 60. In term of optical coupling, above elucidations regarding the flexible guiding portion 5 shown in FIG. 1 apply accordingly.

The system 1 further comprises a control unit 100, e.g. an integrated image acquisition and processing device, which is preferably configured to execute a computer program to generate digital images from image data obtained from the first and second imaging device 4, 6 and process same by image processing algorithms, in particular a first imaging mode and a second imaging mode described in detail further below.

The control unit 100 preferably comprises an acquisition module 105 configured to acquire image data from the first and second imaging device 4, 6, a first processing module 101 configured to process the acquired image data in the first and/or second imaging mode, a second processing module 102 configured to combine, in particular merge, the processed image data, and a third imaging module 103 configured to quantify the merged image data, before single or combined, in particular merged, images are displayed on a display unit 104.

It is noted that the image data processing steps by means of the processing modules 101, 102, 103 are not mandatory, i.e. it is possible to convey acquired image data from the acquisition module 105 to the second processing module 102 to merge, e.g., image data of a first image and image data of a second image without processing the image data in the first and/or second imaging mode. Likewise, it is possible to convey image data to the display unit 104 without merging the image data in the second processing module 102.

Preferably, the control unit 100 further comprises a data storage module 106 configured to store the image data acquired by means of the acquisition module 105 in a database 107 for re-evaluation, documentation purposes or training purposes.

In particular, the control unit 100 is adapted for processing first images, e.g. multi-spectral reflection images, and second images, e.g. marker light images, in parallel and rendering at least one combined image based on at least one first image and at least one second image. The at least one combined image can be processed and rendered in real-time, i.e. with a delay after the image collection such that the delay is negligible in terms of human visual perception, preferably with a delay of less than 500 ms, more preferably less than 100 ms, in particular less than 50 ms.

Providing at least one combined image in real-time may also include providing an image sequence, i.e. a video sequence, of combined images. As an example, the control unit 100 may be configured for generating a video sequence of at least one first image, at least one second image, at least one combined image or a combination thereof.

Additionally or alternatively, spectral collection of image data can be achieved by time-sharing the activation of multiple illumination arrangements of a light source in time-synchronized subsequent full or partial readouts of image data from the first and/or second imaging device 4, 6. Alternatively, spectral decomposition systems, such as prisms, monochromators etc. can be employed.

Figure 3:
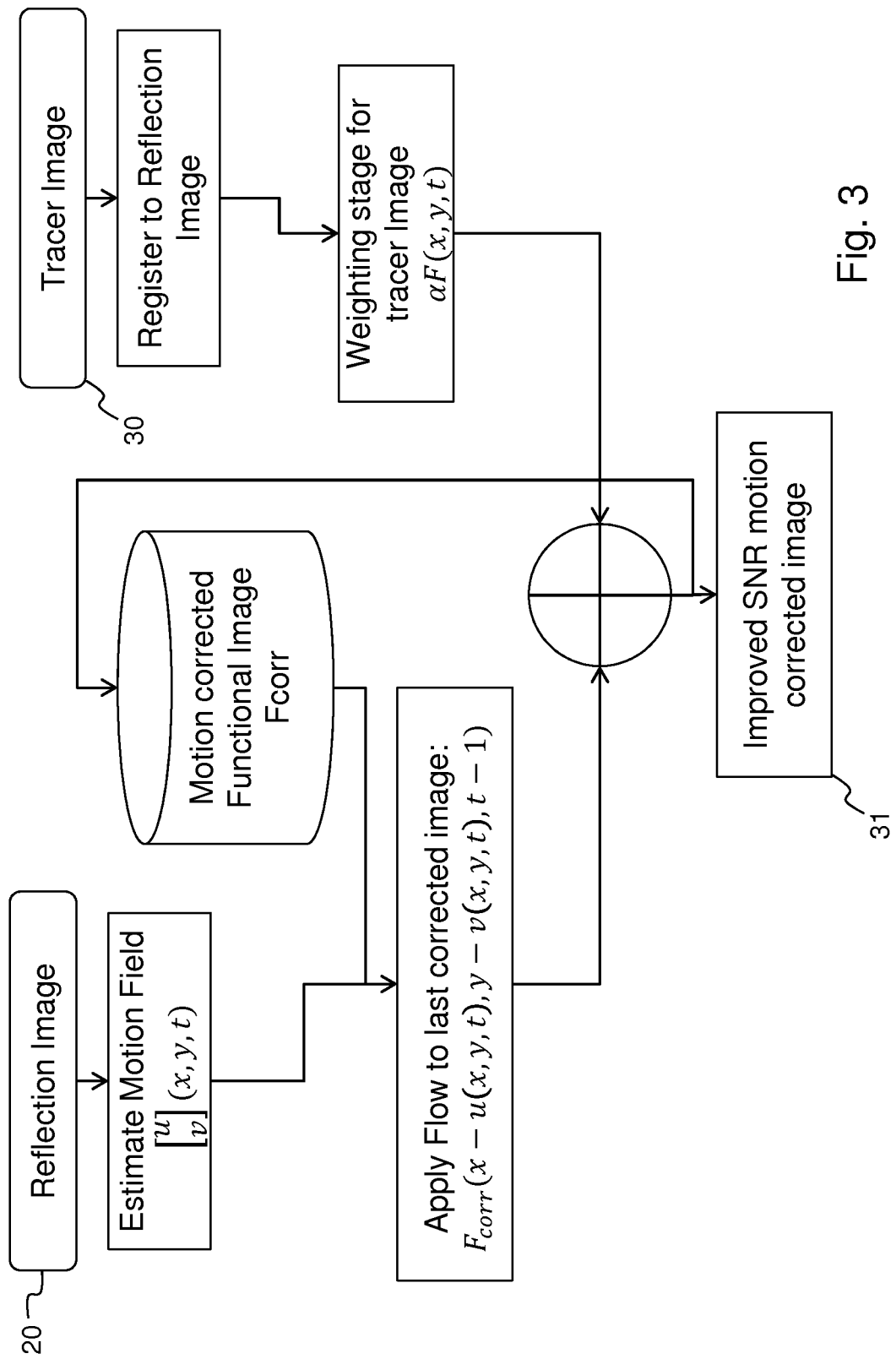
FIG. 3 shows an exemplary schematic of a first imaging mode.

FIG. 3 shows an exemplary schematic of a first imaging mode, also referred to as motion-compensation mode.

In the first imaging mode, image data from first images 20, also referred to as reflection images, obtained by a first imaging device, in particular with high resolution, are utilized to determine, in particular estimate, a two-dimensional motion field characteristic of a movement of a medium relative to an insertion portion or for a movement of portions of the medium relative to further portions of the medium.

Preferably, the motion field is a dense motion field which refers to the description of motion-induced vector components (e.g., distance and direction) of every picture element (pixel) between two subsequently acquired images. More specifically, for every picture element of the image, a 2D vector describes, which point corresponds to its motion-induced related position in the previously acquired image. More specifically, said 2D vectors refer to a tuple of signed rational numbers for the differential offset in the image coordinate reference system.

Also, image data from second images 30, also referred to as tracer images, obtained by a second imaging device with high sensitivity, are registered to the image data from the first images 20.

Subsequently, the image data from the second images 30 is weighted with a, preferably constant, factor α corresponding to the magnitude to which extent recent image data is weighted more important than less recently obtained image data. By applying said factor in an iterative manner, the relative contribution of the single second images decays exponentially with the time that has elapsed since the most recent acquisition of the second image.

The motion-induced changes in the weighted image data are reverted according to the two-dimensional motion field of a single second image 30, resulting in motion-corrected image data of the single second image 30, also referred to as functional image data $F_{corr}$. The motion-corrected image data of the single second image 30 may then be outputted, e.g., on a display device.

Preferably, the motion-corrected image data of at least one second image 30 form a third image 31. Therefore, within the meaning of present disclosure, the expressions "motion-corrected image data of second image 30" and "motion-corrected second image 30" are used synonymously to "image data of third image 31" or "third image 31", respectively.

Preferably, the motion-corrected image data of the single second image 30 may be combined with more recent image data of a further second image 30, thereby virtually prolonging the exposure time of the second imaging device and increasing the signal-to-noise ratio of the further second image 30. Preferably, this process is repeated in an iterative manner, wherein two-dimensional motion fields are calculated from the image data of subsequently acquired first images 20. Said motion-field is utilized to revert the motion-induced effects of the corresponding image data of subsequently acquired second images 30, resulting in a particularly high signal-to-noise ratio of a motion-corrected second image 30 or third image 31, respectively. In particular, the resulting corrected second image 31 now incorporates information of every of the previously acquired single second images 30 in adapted weights (e.g., exponentially smoothed) and therefore depicts an advantageous combination of the sensitivity-challenged and resolution-challenged information.

FIG. 4 shows an exemplary schematic of a second imaging mode, also referred to as dynamic enhancement mode, wherein image data of an acquired first image 20 as shown in FIG. 4(*c*) and image data of an acquired second image 30 as shown in FIG. 4(*a*) are spatially registered such that each portion of the first image 20 corresponds to a portion of the second image 30.

In present example, the first and the second images 20, 30 are acquired by the first imaging device 4 and second imaging device 6 (see FIGS. 1 and 2), respectively, from the same area of interest and preferably at the same time. As apparent from FIG. 4(*c*), the first image 20 is acquired at high resolution such that spatial features and details, e.g. of indicated X-shaped structure with higher contrast, in the area of interest are resolved well. As apparent from FIG. 4(*a*), the second image 30 is acquired at high sensitivity such that features in the area of interest with lower contrast, as exemplarily indicated by a dotted circle, can be resolved well, whereas not all details of the finer X-shaped structure are resolved.

FIG. 4(*d*) and FIG. 4(*b*) show histograms (number of pixels vs. tonal values of the pixels) of the first image 20 and the second image 30, respectively. Due to the high sensitivity of the second imaging device, the left part of the corresponding histogram in FIG. 4(*b*) contains contributions to the histogram which the histogram in FIG. 4(*d*) of the first image 20 lacks. Likewise, due to the high resolution of the first imaging device, the right part of the corresponding histogram in FIG. 4(*d*) contains contributions to the histogram which the histogram in FIG. 4(*b*) of the second image 30 lacks.

The image data of the first and second image may be combined to a third image 32 in a manner such that information contained in the first image 20 obtained at a high resolution and information contained in the second image 30 obtained at a high sensitivity contribute to the third image 32, as shown in FIG. 4(*e*), according to their sensitivity-transfer function. By this means, the first imaging device and the second imaging device supplement each other regarding imaging performance such as resolution and sensitivity. Accordingly, information of the first image 20 and information of the second image 30 supplement each other in the third image 32. Thus, the third image 32 is superior to the first and the second image taken alone.

FIG. 4(*f*) shows a histogram of the third image 32. As the third image comprises information corresponding to both high resolution and high sensitivity, the histogram contains contributions both in the left part and in the right part of the histogram.

The ratio of detectable lowest signal values and highest signal values, which is also referred to as "dynamic range", and the quantification resolution of the analog-to-digital converter for the pixel values (e.g., 16 Bits vs. 12 Bits) is preferably superior in the second image sensor, in comparison to the first image sensor.

Preferably, the second imaging sensor has a higher probability that an incident photon results in an electron, which can be digitized. In other words, the second imaging sensor has a higher sensitivity or quantum efficiency for incident photons than the first sensor.

Preferably, the first imaging sensor and the related optical path enable a superior spatial resolution, e.g., a higher number of resolvable contrast-inducing line-pairs per length in the imaged field of view, compared to the second imaging sensor.

The combination of first and second image to a third image, in which the advantages of the first and second imaging device are combined and/or weaknesses of the first or second imaging device are compensated, preferably affects a DC-offset, a gain, a noise-level, differences in a detection area, spectral-band-differences, and different optical attenuation in the optical path towards the respective sensor, the sensitivity, the dynamic range, and the spatial resolution. Preferably the combination of the first and second image 20, 30 is applied in a way, such that $$F_{corr} = T_1(F_1, par1) + T_2(F_2, par2),$$

where $F_{corr}$ is the final corrected fluorescence image, i.e. the third image 32, $T_1$ and $T_2$ are transfer functions to adjust the intensity information of first image $F_1$ and second image $F_2$ according to a set of parameters $par_1/par_2$ of the transfer function in a way that the more suiting source of information is dominant at the given intensities.

An advantageous transfer function for deciding the weight-factors for merging $F_1$ and $F_2$ is the logistic function $$T(x) = \frac{1}{1 + e^{-k(x-x_0)}},$$

wherein the set of parameters (e.g., $par_1$, $par_2$), the parameter $x_0$ is the cut-point of the logistic function, and the parameter k represents its steepness.

The specific kind of the transfer functions and the corresponding parameters for the transfer functions par1 and par2 have to be calibrated for the specific combination for optical sensors, filter and beam splitters and the like. In a preferred application in medical imaging, the system for endoscopic imaging may be used by executing the following three steps: administering one or more contrast agents or probes, also referred to as marker substances, e.g. molecular probes; optical imaging, in particular multispectral optical imaging; and processing of captured images for real-time display of corrected information.

The administration step is an optional step. It can be omitted, in particular, if the sample already includes at least one marker substance for natural reasons or due to a previous treatment. The at least one first image obtained with the system is also termed "inspection image". The term "inspection image" refers to the fact that the image can be used for finding a particular tissue feature, for diagnosis, for guiding treatment e. g. by a physician and/or by a subsequent image evaluation, or for identification of a suspicious lesion such that efficient guidance and intervention with high specificity can be provided, e.g. an intervention with therapeutic intend.

The at least one second image obtained with the system is also termed "diagnostic image". The diagnostic image may include a map of the object highlighting various object conditions. Similarly the diagnostic image can be used to guide minimally invasive surgical intervention or endoscopically administered biopsies. However, the diagnostic image as such preferably does not deliver the diagnosis.

The term "marker substance" refers to any molecule which can alter the light generated by a light source and emitted towards a material of the object so as to generate contrast. A common example is a fluorochrome which stains perfusion, permeability or specifically binds to a certain target in the object, like target tissue, target cells or certain cell components, like proteins, and which exhibits an interaction with light (UV, VIS and/or IR wavelength ranges) resulting in a specific absorption and/or fluorescence. The concept of use of a marker substance is to highlight one or more tissue characteristics which are altered at a presence of a disease. The marker substance is also called biomarker, probe or contrast agent. It is selected by the skilled person in dependence on the binding properties and the spectral properties thereof. In particular, the marker substance is selected such it targets and reveals a molecular, structural, functional or compositional feature of the tissue which specifically changes in a gradual manner during the disease progress. The presence of the marker substance preferably alters the optical properties of the tissue, e.g. fluorescence or absorbance, in a way that the detected optical signal could even reveal the progress of the disease. The object preferably includes one or more marker substances. If multiple different marker substances are provided, they preferably have different spectroscopic properties. Besides fluorochromes, the marker substances can be absorbing dyes, nanoparticles, polarization shifting moieties, fluorescence resonance energy transfer molecules, Raman particles etc.

The invention claimed is:

1. A system for endoscopic imaging comprising:
   a light source configured to generate light;
   an insertion portion configured to be inserted into an object and comprising a distal end, a proximal end and a light guiding path configured to guide the generated light to the distal end of the insertion portion and to guide light emanating from a medium within the object to the proximal end of the insertion portion;
   a first imaging device mounted at the proximal end of the insertion portion and optically coupled to the light guiding path, the first imaging device comprising a plurality of first detecting elements, the first detecting elements exhibiting a first sensitivity to light and being configured to detect a first part of the light emanating from the medium to obtain at least one first image of the medium exhibiting a first spatial resolution, the at least one first image of the medium comprising at least one of a color image or reflectance image of the medium;
   a flexible guiding portion comprising a distal end and a proximal end, the distal end of the guiding portion being optically coupled to the light guiding path, and being configured to guide a second part of the light emanating from the medium from the distal end of the guiding portion to the proximal end (5a) of the guiding portion;
   a second imaging device provided at the proximal end of the flexible guiding portion and comprising a plurality of second detecting elements, the second detecting elements exhibiting a second sensitivity to light and being configured to detect the second part of the light emanating from the medium to obtain at least one second image of the medium exhibiting a second spatial resolution, the at least one second image of the medium being a fluorescence image of the medium, the second sensitivity of the second detecting elements being higher than the first sensitivity of the first detecting elements and the first spatial resolution of the first image being higher than the second spatial resolution of the second image; and a control unit configured to derive at least one third image of the medium based on image data of the at least one first image of the medium and image data of the at least one second image of the medium by correcting image data of the at least one second image of the medium for motion of the insertion portion and the medium relative to each other based on image data of two subsequently acquired first images of the medium, wherein the motion-corrected image data of the at least one second image form the at least one third image.

2. The system according to claim 1, the control unit being further configured to determine, based on image data of the at least one first image of the medium, a two-dimensional motion field characterizing a velocity of the medium relative to the insertion portion or velocities of different regions of the medium relative to each other.

3. The system according to claim 2, the control unit being further configured to revert a motion-induced relative displacement of image data of the at least one second image based on the two dimensional motion field to obtain the at least one third image of the medium.

4. The system according to claim 2, the control unit being further configured to revert a motion-induced relative displacement of image data in each of two or more successively obtained second images based on the two-dimensional motion field to obtain two or more adapted second images, and to combine the two or more adapted second images to obtain the at least one third image of the medium.

5. The system according to claim 2, the two-dimensional motion field comprising motion-induced vector components, including a distance and direction, of every picture element between the two subsequently acquired first images.

6. The system according to claim 2, the control unit being further configured to weight image data of the second image with a factor the magnitude of which depending on how much recent image data of the second image is, wherein image data of a more recently obtained second image is weighted with a higher factor than image data of a less recently obtained second image.

7. The system according to claim 1, the control unit being further configured to determine, based on image data of at least two successively obtained first images of the medium, a two-dimensional motion field, to revert a motion-induced relative displacement of image data in each of at least two successively obtained second images based on the two-dimensional motion field to obtain two or more adapted second images, and to combine the two or more adapted successively obtained second images to obtain the at least one third image of the medium.

8. The system according to claim 1, the control unit being configured to control the first imaging device and the second imaging device to detect the first part of the light emanating from the medium and the second part of the light emanating from the medium simultaneously.

9. The system according to claim 1, wherein the first part of the light and the second part of the light emanate from the same region of interest of the medium or from overlapping regions of interest of the medium.

10. The system of claim 1, wherein the insertion portion is rigid.

11. A method for processing images generated by a system for endoscopic imaging, wherein the system comprises:

a light source configured to generate light;

an insertion portion configured to be inserted into an object and comprising a distal end, a proximal end and a light guiding path configured to guide the generated light to the distal end of the insertion portion and to guide light emanating from a medium within the object to the proximal end of the insertion portion;

a first imaging device mounted at the proximal end of the insertion portion and optically coupled to the light guiding path, the first imaging device comprising a plurality of first detecting elements, the first detecting elements exhibiting a first sensitivity to light and being configured to detect a first part of the light emanating from the medium to obtain at least one first image of the medium exhibiting a first spatial resolution, the at least one first image of the medium comprising at least one of a color image or a reflectance image of the medium;

a flexible guiding portion comprising a distal end and a proximal end, the distal end of the guiding portion being optically coupled to the light guiding path, and being configured to guide a second part of the light emanating from the medium from the distal end of the guiding portion to the proximal end of the guiding portion; and a second imaging device provided at the proximal end of the flexible guiding portion and comprising a plurality of second detecting elements, the second detecting elements exhibiting a second sensitivity to light and being configured to detect the second part of the light emanating from the medium to obtain at least one second image of the medium exhibiting a second spatial resolution, the at least one second image of the medium being a fluorescence image of the medium, the second sensitivity of the second detecting elements being higher than the first sensitivity of the first detecting elements and the first spatial resolution of the first image being higher than the second spatial resolution of the second image; and wherein the method comprises:

deriving at least one third image of the medium based on image data of the at least one first image of the medium and image data of the at least one second image of the medium by correcting image data of the at least one second image of the medium for motion of the insertion portion and the medium relative to each other based on image data of two subsequently acquired first images of the medium, wherein motion-corrected image data of the at least one second image form the at least one third image.

12. The method of claim 11, wherein the insertion portion is rigid.

* * * * *